US006426098B1

(12) United States Patent
Yang Jr.

(10) Patent No.: US 6,426,098 B1
(45) Date of Patent: *Jul. 30, 2002

(54) HERBAL COMPOSITIONS FOR HEPATIC DISORDERS

(75) Inventor: Yi Fan Yang Jr., Surry Hills (AU)

(73) Assignee: Cathay Herbal Laboratories, Surrey Hills (AU)

(*) Notice: Subject to any disclaimer, the term of this patent is extended or adjusted under 35 U.S.C. 154(b) by 0 days.

This patent is subject to a terminal disclaimer.

(21) Appl. No.: 09/679,400

(22) Filed: Oct. 3, 2000

Related U.S. Application Data

(63) Continuation of application No. 08/983,616, filed as application No. PCT/AU96/00434 on Jul. 10, 1996, now Pat. No. 6,126,942.

(30) Foreign Application Priority Data

Jul. 10, 1995 (AU) .............................................. PN 4111

(51) Int. Cl.[7] .............................................. A61K 35/78
(52) U.S. Cl. ........................ 424/728; 424/725; 424/740; 424/756; 424/764; 424/773; 424/777; 514/893; 514/894
(58) Field of Search ................................. 424/725, 728, 424/773, 740, 777, 756, 464; 514/893, 894

(56) References Cited

U.S. PATENT DOCUMENTS 4,886,666 A * 12/1989 Liu

FOREIGN PATENT DOCUMENTS

| CN | 1101281 | * | 4/1989 |
| JP | 2103016 | * | 5/1987 |
| JP | 1102092 | * | 4/1989 |

OTHER PUBLICATIONS

Chung Kuo Chung Hsi I Chieh Ho Tsa Chi (China) Sep. 1993 13(9) Xiong L L "Therapeutic effects of combined therapy of Salvia Miltiorrhizae and *Polyporus umbellatus* polysaccharide in the treatment of chronic hepatitis B." pp. 533–535, 516–517 Abstract.

Chung Hsi I Chieh Ho Tsa Chih (China) Apr. 1991 11(4) pp. 225–226 (Abstract) Zhang, Y.H. et al. "Effect of *Polyporus umbellatus* polysaccharide on function of macrophages in the peritoneal cavities of mice liver with lesions".

Chung Hsi I Chieh Ho Tsa Chi (China) Feb. 1991 11(2) pp. 102–104 (Abstract) Qi, X.G., "Protective mechanism of *Salvia miltiorrhiza* and *Paeonia lactiflora* for experimental liver damage".

Chung Kuo Chung Yao Tsa Chih (China) Dec. 1992 17(12) pp. 749–751 (Abstract).

Yu, Z.P. et al. "Effects of *Salvia miltiorrhiza* Bunge on isolated perfused liver and portal vein of rats".

Journal of Ethnopharmacology 1987 19 pp. 103–110, Ling–Ling Yang et al. "Antihepatoxic Actions of Formosan Plant Drugs".

Cancer Letters, 1986, 30, pp. 143–151. Hajime Ohigashi et al. "Search for Possible Antitumour Promotors by Inhibition of the 12–0–Tetradecanoylphorbol–13–Acetate–Induced Epstein–Barr Virus Activation; Ursolic Acid and Oleanolic Acid from an Anti–inflammatory Chinese Medicinal Plant, *Glechoma hederaceae L.*".

Planta Medica, 1994, vol. 60, pp. 414–416 Yoshikazu Kondo et al. "Suppression of Chemically and Immunologically Induced Hepatic Injuries by Gentiopicroside In Mice".

Planta Medica, 1988, vol. 54, pp. 413–414, Shean Farn Yeh et al. "Effects of Anthraquinones of *Polygonum cuspidatum* on HL–60 Cells".

A Textbook of Natural Medicine, 1993, vol. I, Joseph E. Pizzorno and Michael T. Murray, "Glycyrrhiza" V glycyr 3, Bastyr College Publications; Seattle, Washington.

Medicinal Plants in China, 1989, World Health Organization (WHO) Regional Publications Western Pacific Series No. 2, Manila, pp. 30, 42, 48, 71, 84, 96, 97, 139, 150.

Healing with Chinese Herbs, 1990, Richard Hyatt, Healing Arts Press; Rochester, Vermont, pp. 113, 122, 133, 134, 139, 142.

Chung Hsi I Chieh Ho Tsa Chih (China), Aug. 1987, vol. 7(8), pp. 483–484, Wang, S.L., et al, "Effects of *Crataegus pinnatifidae, Astragalus membranaceus* and *Acanthopanax senticosus* on cholesterol metabolism in the guinea pig." (Abstract).

Indian Journal of Exp Biol, Jul. 1989, vol. 27(7), pp. 631–634, Dua et al., "Adaptogeaic activity of Indian *Panax pseudoginseng*".

* cited by examiner

Primary Examiner—Christopher R. Tate
(74) Attorney, Agent, or Firm—Fenwick & West, LLP

(57) ABSTRACT

Compositions for treating hepatic disorders via oral or parenteral administration include *Salvia miltiorrhiza* and *Polyporus umbellatus* in proportions of about 1:1 to about 5:1, and may comprise from about 6% to about 30% of the total weight of the composition which may also include other herbs such as *Curcuma longa, Astragalus membranaceus, Loranthus parasiticus* and *Polygonum cuspidatum*.

22 Claims, No Drawings

HERBAL COMPOSITIONS FOR HEPATIC DISORDERS

RELATED APPLICATION

This application is a continuation of application Ser. No. 08/983,616, entitled "Herbal Composition for Hepatic Disorders," filed on Aug. 17, 1988, by Yi Fan Yang, which is now U.S. Pat. No. 6,126,942, and which is entitled to priority under 35U.S.C. §371 from application PCT/AU96/00434 having international filing date of Jul. 10, 1996, based upon original Australian application PN 4111, filed Jul. 10, 1995.

TECHNICAL FIELD

This invention relates to a new medicinal compositions and methods of treating hepatic disorders.

BACKGROUND ART

Hepatic disorders, in particular those caused by viral infections, are a major health problem and the successful treatment of hepatic diseases poses a great challenge to the medical profession. With respect to hepatic diseases caused by viral infection, currently patients in advanced stages of the infection cycle (chronic hepatitis) with, for example, hepatitis C virus are treated with Interferon ("IFN") with only about 25% success rate. IFN is not readily available to patients and a six-month course of IFN therapy costs about $3000. It also gives rise to several side-effects such as severe flu symptoms, lethargy, hair loss and undesirable tastes in the mouth. IFN acts against the virus via the immune system and does not reverse any physiological abnormalities or damage caused by the infection e.g. hepatic cirrhosis, diminished spleen function, etc. Furthermore, as there is a number of hepatic disorders which are not caused by viral infection, the administration of INF to patients with non-viral hepatic disorders would be ineffective.

It is an object of the present invention to provide an effective method of and medication for, treatment of both viral and non-viral hepatic disorders which avoids or at least ameliorates one or more of the disadvantages of current treatments.

SUMMARY OF THE INVENTION

According to a first aspect, the invention consists in a composition comprising the herbs *Salvia miltiorrhiza* and *Polyporus umbellatus*, or extracts thereof.

In the preferred embodiment the invention consists in the composition which further comprises at lest one of the herbs *Curcuma longa, Astragalus membranaceus, Loranthus parasiticus* and *Polygonum cuspidatum*, or extracts thereof.

In another preferred embodiment the invention consists in a composition which further comprises at least one of the herbs *Poria cocos, Artemisia capillaries, Taraxacum mongolicum, Paeonia lactiflora, Panax pseudogiseng, Bupleurum falcatum, Crataegus pinnatifida, Glechoma longituba, Codonopsis pilosula, Lycium barbarum, Zizyphus jujuba, Gentiana manshurica* and *Glycyrrhiza uralensis,* or extracts thereof.

According to a second aspect the invention consists in a composition comprising the herbs *Salvia miltiorrhiza, Polyporus umbellatus, Poria cocos, Artemisia capillaries, Taraxacum mongolicum, Paeonia lactiflora, Panax pseudoginseng, Bupleurum falcatum, Crataegus pinnatifida, Curcuma longa, Glechoma longituba, Astragalus membranaceus, Codonopsis pilosula, Loranthus parasiticus, Lycium barbarum, Polygonum cuspidatum, Zizyphus jujuba, Gentiana manshurica* and *Glycyrrhiza uralensis,* or extracts thereof.

According to a third aspect, the invention consists in a method of treating hepatic disorders comprising the step of administering to a patient requiring such treatment any one of the compositions described above.

Preferably, the hepatic disorder treated is a non-viral hepatic disorder such as alcoholic hepatitis, cirrhosis or autoimmune liver disease.

More preferably the hepatic disorder treated is caused by a viral infection such as hepatitis virus A, B or C infection.

The treatment can be therapeutic or prophylactic, and may be administered orally or parenterally. The parenteral route could be topical, intravenous or subcutaneous. The treatment may be delivered in a single bolus dose, multiple doses or via a slow release device or a depot.

DESCRIPTION OF THE PREFERRED EMBODIMENT

In a preferred embodiment of the invention, the composition of the invention comprises *Salvia miltiorrhiza* and *Polyporus umbellatus* in the proportion of from 1:1 to 1:5 or 5:1. For example, these herbs may each comprise from 6 to 30% of the total weight of the herbal composition, the balance being made up for example by other herbs, preferably *Curcuma longa* (2–10%). *Astragalus membranaceus* (5–30%), *Loranthus parasiticus* (5–30%) and *Polygonum cuspidatum* (3–20%).

Although the administration of a composition containing only Salvia and Polyporus will be effective in treating chronic hepatitis, the synergism between all the herbs render the administration of a combination containing each herb desirable.

Thus, in a more preferred embodiment, the composition comprises each herb combined in the proportions given in Table 1.

Various parts of each herb may be used and these include the root, stem, fruit or whole plant or tuber.

The availability of the herbs and ease of concentrating the extracts provides a cheaper, alternative medicine which also does not give rise to undesirable side-effects. There is also a higher incidence of cure in that liver cirrhosis may be reversed and hepatic enzyme levels and microcirculation may be normalised, thus rendering this form of treatment applicable not only to hepatic disorders caused by virus infection but also those disorders caused by other agents and causes which can compromise liver function and microcirculation.

The invention will now be described with reference to the following example to illustrate a preferred embodiment only and does not serve to limit the invention.

EXAMPLE 1

One method of preparing the compositions of the invention is to mix the cut, ground or powdered herbs listed in Table 1 and boil the mixture in a vat. The liquid is thus concentrated into a paste which can subsequently be processed further into tablets averaging about 170 mg each, using procedures which conform to standard, General Manufactured Products (GMP) guidelines.

TABLE 1

Medicinal composition comprising herbal extracts in pill-form

| Powdered Herbs | Weight |
| --- | --- |
| *Polyporus umbellatus* root | 16 mg |
| *Salvia miltiorrhiza* root | 14 mg |
| *Artemisia capillaries* Thumb | 14 mg |
| *Poria cocos* root | 12 mg |
| *Taraxacum mongolicum* plant | 12 mg |
| *Paeonia lactiflora* root | 10 mg |
| *Astragalus membranaceus* root | 10 mg |
| *Loranthus parasiticus* stem | 10 mg |
| *Glechoma longituba* plant | 9 mg |
| *Codonopsis pilosula* root | 9 mg |
| *Polygorrum cuspidanum* root | 9 mg |
| *Gentiana manshurica* plant | 9 mg |
| *Bupleurum falcatum* root | 7 mg |
| *Crataegus pinnarifida* fruit | 7 mg |
| *Lycium barbarum* fruit | 7 mg |
| *Zizyphus jujuba* fruit | 7 mg |
| *Curcuma longa* tuber | 5 mg |
| *Panax pseudoginseng* root | 3 mg |
| *Glycyrrhiza uralensis* root (colouring/coating) | 5 mg |

Consumption of 8 tablets three times daily, 30–60 minutes prior to meals with warm water is recommended for adults. Children may be prescribed half the adult dosage. The dosage and the formulation may be varied according to the condition treated and the concentration of active ingredients used in each dose. Thus, the dosage may range from 3 to 10 tablets three times daily, or more or less frequently as required. The compositions may also be administered as a liquid or in the form of a slow release formulation.

EXAMPLE 2

An alternative method of preparing the compositions of the invention is to powder the herbs listed in Table 1 by crushing and grinding each herb after drying it in a machine in a known, conventional manner. The individual components are then formulated into tablets.

EXAMPLE 3

A tablet form of the composition prepared according to Example 1 was evaluated in patients with chronic hepatitis C (CHCV) using a double-blind, randomised placebo controlled protocol. Treatment involved 5 tablets tds for 6 months with monthly assessment by a hepatologist and traditional Chinese medicine specialist. 58 patients wee assessed, 43 randomised to treatment and 40 completed therapy.

| Results | Treated Group | Placebo Group |
| --- | --- | --- |
| (n) Age (yrs) | 10; 40.4 | 20; 40.9 |
| Male % | 59.1 | 59.1 |
| Duration of HCV (mths) | 92 | 83 |
| Alcohol g/d; Past interferon | 20; | 20; |
| Initial/final ALT | 120/82 | 102/102 |

Treatment with the composition of the present invention rested in a significant (p<0.03) fall in ALT whereas treatment with placebo did not (Wilcoxon matched pairs signed rank test for non-parametric date). 4 patients in the treatment group normalised their ALT but relapsed on cessation of drug. Treatment had no effect on ALP, Haemoglobin, WCC and platelets. The results of the study demonstrate that the composition was capable of modifying disease activity in CHCV. Further studies of the treatment on HCV-RNA and histological changes are supported by these preliminary results.

A person skilled in the art will understand that the therapeutic effects of the composition result from a plurality of active agents in each herb which when combined, act synergistically to enhance efficacy. It will also be understood that compositions comprising all or a selection of such active agents, preferably in pure form, are also contemplated herein, as are liquid formulations of the composition and formulations which are suitable for slow release administration. Thus it will be understood that the compositions of the invention can be administered orally, intravenously, subcutaneously, topically or by other known means.

The compositions are effective in treating hepatic disorders generally, irrespective of their aetiology since the compositions act at least in part to improve liver function and microcirculation. The compositions may also exert their effect prophylactically, by preventing or minimising the adverse effects of viral infection or the action of other agents which cause liver dysfunction. Therefore, the treatment of hepatic disorders caused by viral infection, autoimmune reactions, drug intake and the like are contemplated herein.

The invention may be embodied in various other forms which are understood by those skilled in the art.

What is claimed is:

1. A medicinal composition suitable for treating hepatic disorders comprising the herbs *Salvia miltiorrhiza* root, *Polyporus umbellatus* root, *Poria cocos* root, *Artemisia capillaries* Thumb. plant, *Taxaxacum mongolicum* plant, *Paeonia lactiflora* root, *Panax pseudoginseng* root, *Bupleurum falcatum* root, *Crataegus pinnatifida* fruit, *Curcuma longa* tuber, *Glechoma longituba* plant, *Astragalus membranaceus* root, *Codonopsis pitosuta* root, *Loranthus parasiticus* stem, *Lycium barbarum* fruit, *Polygonum cuspidatum* root, *Zizyphus jujuba* fruit, *Gentiana manshurica* plant and *Glycyrrhiza uralensis* root, or extracts thereof.

2. A composition according to claim 1 wherein the composition comprises the herbal extracts in the form of a tablet.

3. A composition according to claim 1 wherein the composition comprises the herbal extracts in the form of a liquid.

4. A composition according to claim 1 wherein the *Salvia miltiorrhiza* root and *Polyporus umbellatus* root each comprise from 6 to 30% of the total weight of the composition.

5. A composition of herbs or the extracts thereof according to claim 1 comprising approximately 14 parts *Salvia miltiorrhiza* root, 16 parts *polyporus umbellatus* root, 12 parts *Poria cocos* root, 14 parts *Artemisia capillaries* Thumb. plant, 12 parts *Taraxacum mongolicum* plant, 10 parts *Paeonia lactiflora* root, 3 parts *Panax pseudoginseng* root, 7 parts *Bupleurum falcatum* root, 7 parts *Crataegus pinnatifida* fruit, 5 parts *Curcuma longa* tuber, 9 parts *Glechoma longituba* plant, 10 parts *Astragalus membranaceus* root, 9 parts *Codonopsis pilosula* root, 10 parts *Loranthus parasiticus* stem, 7 parts *Lycium barbarum* fruit, 9 parts *Polygonum cuspidatum* root, 7 parts *Zizyphus jujuba* fruit, 9 parts *Gentiana manshurica* plant and 5 parts *Glycyrrhiza uralensis* root.

6. A composition for treating a hepatic disorder comprising effective amounts of the herbs *Salvia miltiorrhiza* root, *Polyporus umbellatus* root, *Poria cocos* root, *Artemisia capillaries* Thumb. plant, *Taraxacum mongolicum* plant, *Paeonia lactiflora* root, *Panax pseudoginseng* root, *Bupleurum falcatum* root, *Crataegus pinnatifida* fruit, *Curcuma longa* tuber, *Glechoma longituba* plant, *Astragalus mem-*

*branaceus* root, *Codonopsis pilosula* root, *Loranthus parasiticus* stem, *Lycium barbarum* fruit, *Polygonum cuspidatum* root, *Zizyphus jujuba* fruit, *Gentiana manshurica* plant and *Glycyrrhiza uralensis* root, or liquor extracts thereof.

7. A composition according to claim 6 wherein the composition comprises the herbal extracts in the form of a tablet.

8. A composition according to claim 6 wherein the composition comprises the herbal extracts in the form of a liquid.

9. A composition according to claim 6 wherein the *Salvia miltiorrhiza* root and *Polyporus umbellatus* root each comprise from 6 to 30% of the total weight of the composition.

10. A method of treating a hepatic disorder comprising the administration to a patient requiring such treatment an effective amount of a composition according to claim 6.

11. A method according to claim 10 wherein the hepatic disorder is caused by a virus infection.

12. A method according to claim 11 wherein the virus infection is a hepatitis C virus infection.

13. A method according to claim 11 wherein the infection is in the form of chronic hepatitis.

14. A method according to claim 10 wherein the hepatic disorder is non-viral hepatitis.

15. A method according to claim 10 wherein the hepatic disorder is associated with an abnormality in hepatic microcirculation.

16. A method according to claim 10 wherein the hepatic disorder is associated with cirrhosis.

17. A method according to claim 16 wherein the composition is administered orally.

18. A method according to claim 10 wherein the composition is administered parenterally.

19. A method according to claim 10 wherein the treatment is therapeutic.

20. A method according to claim 10 wherein the treatment is prophylactic.

21. A method or preparing a medicinal composition for treating a hepatic disorder comprising the steps of:

a. mixing effective amounts of the following cut, ground or powdered herbs: *Salvia miltiorrhiza* root, *Polyporus umbellatus* root, *Poria cocos* root, *Artemisia capillaries* Thumb. plant, *Taraxacum mongolicum* plant, *Paeonia lactiflora* root, *Panax pseudoginseng* root, *Bupleurum falcatum* root, *Crataegus pinnatifida* fruit, *Curcuma longa* tuber, *Glechoma longituba* plant, *Astragalus membranaceus* root, *Codonopsis pilosula* root, *Loranthus parasiticus* stem, *Lycium barbarum* fruit, *Polygonum cuspidatum* root, *Zizyphus jujuba* fruit, *Gentiana manshurica* plant and *Glycyrrhiza uralensis* root, b. boiling the mixture to obtain a concentrated liquor, and c. collecting the concentrated liquor.

22. A method according to claim 21 further comprising the steps of concentrating said liquor into a paste and formulating said paste into tablets.

* * * * *

UNITED STATES PATENT AND TRADEMARK OFFICE
CERTIFICATE OF CORRECTION

PATENT NO.    : 6,426,098 B1                                                                Page 1 of 1
DATED         : July 30, 2002
INVENTOR(S)   : Yi Fan Yang Jr.

It is certified that error appears in the above-identified patent and that said Letters Patent is hereby corrected as shown below:

Column 6,
Line 18, delete "stern" and replace with -- stem --

Signed and Sealed this

Third Day of December, 2002

JAMES E. ROGAN
*Director of the United States Patent and Trademark Office*